United States Patent [19]

Johnson

[11] 4,140,863
[45] Feb. 20, 1979

[54] 9,11-DIHALO-PG$_2$ COMPOUNDS

[75] Inventor: Roy A. Johnson, Kalamazoo, Mich.

[73] Assignee: The Upjohn Company, Kalamazoo, Mich.

[21] Appl. No.: 807,480

[22] Filed: Jun. 17, 1977

[51] Int. Cl.$^2$ ............................................. C07C 177/00
[52] U.S. Cl. ............................ 560/121; 260/239 PF; 260/326.4; 260/556 R; 260/556 AR; 260/408; 260/557 R; 260/557 D; 260/559 B; 260/559 R; 429/365; 429/317; 544/391; 544/551.6; 562/444; 562/465; 546/226; 546/314; 560/557; 568/838; 568/807; 568/645; 568/669; 542/429; 542/408; 560/503
[58] Field of Search .................. 560/27, 55, 60, 62, 560/121; 260/408, 514 D

[56] References Cited

U.S. PATENT DOCUMENTS 3,997,587  12/1976  Muchowski et al. .................. 260/468

Primary Examiner—Robert Gerstl
Attorney, Agent, or Firm—Robert A. Armitage

[57] ABSTRACT

The present invention relates to certain 9,11-dideoxy-PGF-type compounds wherein the C-9 and C-11 carbon atoms are substituted by halogen. In particular, 9,11-chloro-, 9,11-bromo-, and 9,11-iodo-9,11-dideoxy-PGF compounds are disclosed.

These compounds are particularly useful for numerous pharmacological purposes, based on their ability to stimulate mammalian smooth muscle tissue.

33 Claims, No Drawings

9,11-DIHALO-PG$_2$ COMPOUNDS

BACKGROUND OF THE INVENTION

The present invention provides novel compositions of matter and a method for their production. In particular the present invention provides certain 9,11-halo-9,11-dideoxy-PGF-type compounds, which are disclosed herein as structural and pharmacological analogs of naturally-occurring prostaglandin F compounds (e.g., prostaglandin F$_1\alpha$, prostaglandin F$_2\alpha$, and prostaglandin F$_3\alpha$).

The prostaglandins, as well as numerous of their structural analogs, are known in the art as extremely potent pharmacological agents, rendering them useful for a wide variety of pharmacological purposes.

Such prostaglandins and prostaglandin analogs can be characterized as derivatives of prostanoic acid which has the following structural formula and carbon atom numbering.

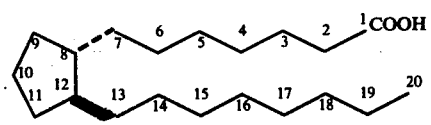

With reference to the above formula, the broken line attachments refer to substituents in the alpha configuration, i.e., below the plane of the cyclopentane ring and heavy solid lines indicate substituents in the beta configuration, i.e., above the plane of the cyclopentane ring. Moreover, the use of wavy lines herein ($\sim$) will represent attachment of substituents in each of the alpha or beta configuration or alternatively attachment in a mixture of alpha and beta configurations.

The prostaglandins, such as PGF$_2\alpha$, i.e.,

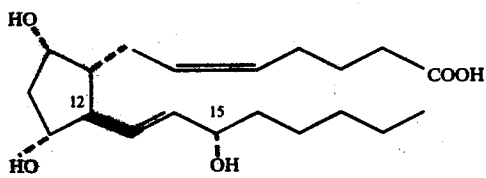

exhibit hydroxylation at the C-15 position of the 12-beta side chain. This side chain hydroxyl at C-15 of PGF$_{2\alpha}$ is in the S configuration. As used herein expressions such as C-15 and the like refer to the carbon atom in a prostaglandin or prostaglandin analog which is in the position corresponding to the position of the same number in prostanoic acid.

Molecules of the prostaglandins, having several centers of asymmetry, can exist in either racemic or optically active forms. Of the two enantiomeric forms of the prostaglandins, the formulas herein make reference to that enantiomeric form which is of the same stereochemical configuration as prostaglandins obtained from mammalian sources. See for example Bergström, et al., Pharmacological Review 20:1 (1968).

Moreover, formulas describing prostaglandin analogs herein shall refer to the enantiomeric form of such analogs which are of the same relative configuration as the prostaglandins obtained from mammalian tissues.

Further, for convenience hereafter the term prostaglandin or "PG" will mean the optically active form of the prostaglandin thereby referred to with the same absolute configuration as obtained from mammalian sources. When reference is made to a racemic form of such prostaglandins, the word "racemic" or "dl" will precede the prostaglandin name. The term "prostaglandin-type" (PG-type) product as used herein will refer to any cyclopentane derivative which is useful for pharmacological purposes. The term "prostaglandin-type intermediate," as used herein, refers to any cyclopentane derivative useful in preparing a prostaglandin-type product. The term "prostaglandin analog" as used herein represents that stereoisomer of a prostaglandin-type product which is of the same relative configuration as the corresponding prostaglandin obtained from mammalian tissues or a mixture comprising such stereoisomers and its enantiomer. In particular, where a formula is used to depict a prostaglandin-type compound herein, the term "prostaglandin analog" refers to the compound of that formula or a mixture comprising that compound and the enantiomer thereof.

Numerous prostaglandins and prostaglandin analogs are known in the art, including prostaglandin analogs wherein the hydrogen present at C-2, C-9, C-14, and C-16, for example, has been replaced by halogen. See, for example, U.S. Pat. No. 4,021,477, describing 14-halo prostaglandin analogs; U.S. Pat. No. 3,997,587, describing 9-fluoro prostaglandin analogs; U.S. Pat. No. 3,001,300, describing 2-fluoro prostaglandin analogs; and U.S. Pat. No. 3,962,293, describing 16-fluoro prostaglandin analogs. See also U.S. Pat. No. 3,755,426 (10-halo-PG's).

SUMMARY OF THE INVENTION

The present invention provides:
a prostaglandin analog of the formula

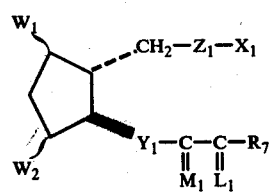

III wherein W$_1$ and W$_2$ are chloro, bromo or iodo, being the same;
wherein Y$_1$ is trans-CH=CH—, —C≡C—, or —CH$_2$CH$_2$—;
wherein M$_1$ is

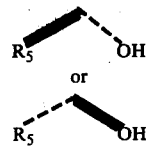

wherein R$_5$ is hydrogen or methyl;
wherein L$_1$ is

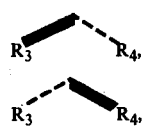

or a mixture of

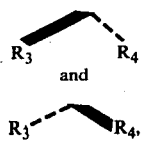

wherein $R_3$ and $R_4$ are hydrogen, methyl, or fluoro, being the same or different, with the proviso that one of $R_3$ and $R_4$ is fluoro only when the other is hydrogen or fluoro;

wherein $Z_1$ is
(1) cis—$CH{=}CH$—$CH_2$—$(CH_2)_g$—$CH_2$—,
(2) cis—$CH{=}CH$—$CH_2$—$(CH_2)_g$—$CF_2$—,
(3) cis—$CH_2$—$CH{=}CH$—$(CH_2)_g$—$CH_2$—,
(4) —$(CH_2)_3$—$(CH_2)_g$—$CH_2$—,
(5) —$(CH_2)_3$—$(CH_2)_g$—$CF_2$—,
(6) —$CH_2$—$O$—$CH_2$—$(CH_2)_g$—$CH_2$—,
(7) —$C{\equiv}C$—$CH_2$—$(CH_2)_g$—$CH_2$—,
(8) —$CH_2$—$C{\equiv}C$—$(CH_2)_g$—$CH_2$—,

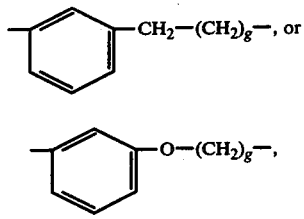

(9)

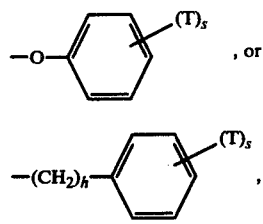

(10)

wherein g is one, 2, or 3;
wherein $R_7$ is
(1) —$(CH_2)_m$—$CH_3$,

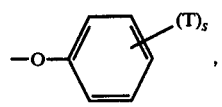

(2)

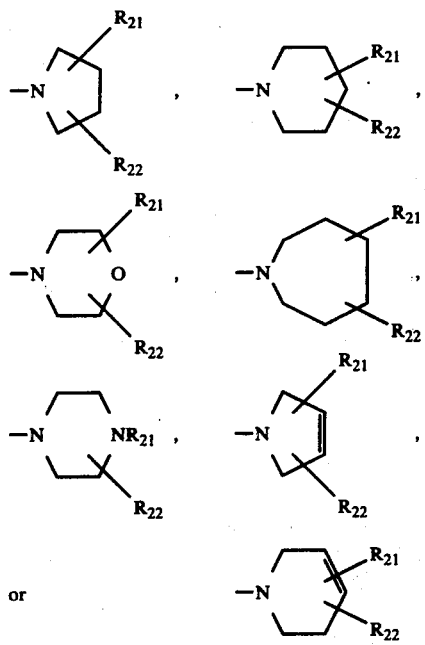

(3)

wherein h is zero, one, 2, or 3, inclusive;
wherein m is one to 5, inclusive, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

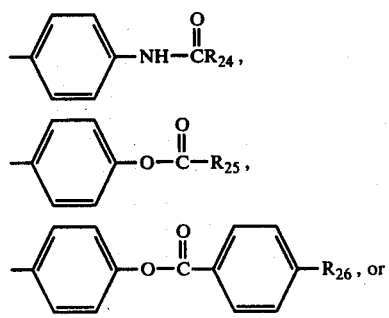

wherein T and s are as defined above, only when $R_3$ and $R_4$ are hydrogen or methyl, being the same or different; and
wherein $X_1$ is
(1) —$COOR_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
(2) —$CH_2OH$,
(3) —$CH_2NL_2L_3$, wherein $L_2$ and $L_3$ are hydrogen, alkyl of one to 4 carbon atoms, inclusive, or —$COOR_1$, wherein $R_1$ is as defined above;
(4) —$COL_4$, wherein $L_4$ is
(a) amino of the formula —$NR_{21}R_{22}$, wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;
(b) cycloamino selected from the group consisting of wherein $R_{21}$ and $R_{22}$ are as defined above;
(c) carbonylamino of the formula —$NR_{23}COR_{21}$, wherein $R_{23}$ is hydrogen or alkyl of one to 4 carbon atoms and $R_{21}$ is as defined above;
(d) sulfonylamino of the formula —$NR_{23}SO_2R_{21}$, wherein $R_{21}$ and $R_{23}$ are as defined above; or
(5) —$COOL_5$, wherein $L_5$ is p-substituted phenyl selected from the group consisting of -continued

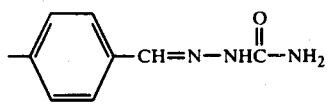

wherein $R_{24}$ is methyl, phenyl, acetamidophenyl, benzamidophenyl, or $-NH_2$; $R_{25}$ is methyl, phenyl, $-NH_2$, or methoxy; and $R_{26}$ is hydrogen or acetamido.

For convenience, the novel prostaglandin analogs described above will be referred to by the trivial, art-recognized system of nomenclature described by N. A. Nelson, Journal of Medicinal Chemistry, 17, 911 (1974). Accordingly, 9α,11α-dichloro-9,11-dideoxy-16-phenyl-17,18,19,20-tetranor-PGF$_2$, methyl ester is represented by formula III, above, when $X_1$ is $-COOCH_3$, $Z_1$ is cis-CH=CH-(CH$_2$)$_5$-, $Y_1$ is trans-CH=CH-, $R_3$, $R_4$, and $R_5$ are all hydrogen and the hydroxy of the $M_1$ moiety is in the alpha configuration, $R_7$ is phenyl, and $W_1$ and $W_2$ are α-chloro. The C-15 epimer of the compound named above (15-epi-9α,11α-dichloro-9,11-dideoxy-16-phenyl-17,18,19,20-tetranor-PGF$_2$, methyl ester) is represented above when the hydroxy of the $M_1$ moiety is in the beta configuration.

The side-chain hydroxy at C-15 in the above formulas is in S or R configuration, as determined by the Cahn-Ingold-Prelog sequence rules. See J. Chem. Ed. 41:16 (1964). See, also, Nature 212, 38 (1966) for discussion of the stereochemistry of the prostaglandins. See particularly U.S. Ser. No. 682,848 for description of the various conventions with respect to the stereochemistry at C-15 as employed herein.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

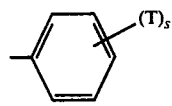

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-(di-fluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, o-, m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro(5- or 6-)methylphenyl.

Amides within the scope of amino groups of the formula $-NR_{21}R_{22}$ are the unsubstituted amide ($-NH_2$), methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Still further examples are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Still further examples are benzylamide, 2-phenylethylamide, 2-phenylethylamide, N-methyl-N-benzylamide, and dibenzylamide. Still further examples are anilide, p-chloroanilide, m-chloroanilide, 2,4-dichloroanilide, 2,4,6-trichloroanilide, p-methylanilide, m-methylanilide, p-ethylanilide, t-butylanilide, p-carboxyanilide, and p-methoxycarbonylanilide.

Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

Amides within the scope of carbonylamino of the formula $-NR_{23}COR_{21}$ are methylcarbonylamide, ethylcarbonylamide, phenylcarbonylamide, and benzylcarbonylamide. Amides within the scope of sulfonylamino of the formula $-NR_{23}SO_2R_{21}$ are methylsulfonylamide, ethylsulfonylamide, phenylsulfonylamide, p-tolylsulfonylamide, and benzylsulfonylamide.

Substituted phenyl esters within the scope of the p-substituted phenyl groups described above are p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

The novel prostaglandin analogs of this invention correspond to the naturally occurring prostaglandins in that the novel prostaglandin analogs are capable of stimulating smooth muscle (as shown by tests, for example, on the gerbil colon).

Because of this biological response, these novel PG analogs are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The novel prostaglandin analogs are also highly active in potentiating other known smooth muscle stimulators, for example, oxytocic agents, e.g., oxytocin, and the various ergot alkaloids including derivatives and analogs thereof. Therefore, these compounds, for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the novel prostaglandin analog is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

Another aspect of the use of the novel prostaglandin analogs of this invention, especially the preferred PG analogs defined hereinbelow, is that these novel PG analogs are administered effectively orally, sublingually, intravaginally, buccally, or rectally, in addition to the intravenous, intramuscular, or subcutaneous injection or infusion methods of administration. These alternate routes of administration are advantageous because they facilitate maintaining uniform levels of these compounds in the body with fewer, shorter, or smaller doses and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For that purpose, it is preferred because of increased water solubility that when $X_1$ is —$COOR_1$, that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

When $X_1$ is —$COOR_1$, the novel PG analogs so described are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

To obtain the optimum combination of biological response specificity, potency, and duration of activity, certain novel prostaglandin analogs within the scope of this invention are preferred in that they exhibit increased potency, duration of selectivity of action, provide more easily stabilized pharmacological formulations, or exhibit a decreased toxicity at the appropriate therapeutic or prophylactic dose. Accordingly, the preferred compounds herein include those compounds wherein g is 3 or 1, most especially 1, are preferred.

In cases where increased pharmacological potency is desired, those compounds wherein the C-15 hydroxy is of the "alpha" configuration are especially preferred. With regard to the various substituents at C-15 and C-16, it is preferred that at least one of $R_3$, $R_4$, and $R_5$ be hydrogen. Further, in the event one of $R_3$ and $R_4$ is methyl or fluoro, it is preferred that $R_3$ and $R_4$ both be methyl or fluoro, respectively.

For those compounds herein where $Y_1$ is cis—CH=CH— or —C≡C—, those compounds wherein $R_3$, $R_4$, and $R_5$ are all hydrogen are preferred.

For the ω-aryl (i.e., where $R_7$ is aryl) compounds herein, preferred compounds are those wherein s is zero or one and T is chloro, fluoro or trifluoromethyl.

Regarding the nature of the C-2 substitution for the novel carboxyamides disclosed herein, the preferred amido substituents are those wherein $R_{21}$ and $R_{22}$ are preferably hydrogen or alkyl of 1 to 8 carbon atoms, inclusive, being the same or different, preferably with the total number of carbon atoms in $R_{21}$ and $R_{22}$ being less than or equal to 8. More especially preferred are those carboxyamide substituents wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to four.

For convenience in preparation and use, the amino group —$NH_2$ is most especially preferred.

With regard to the various cycloamino groups described above, preferred cycloamino groups are those wherein the $R_{21}$ and $R_{22}$ substituents represent the preferred values therefor as described for the acyclic amino groups above. Most preferably, $R_{21}$ and $R_{22}$ are both hydrogen.

With regard to the carbonylamino groups described above, $R_{23}$ is preferably hydrogen and $R_{21}$ is preferably alkyl of one to 8 carbon atoms, inclusive. More preferably, $R_{21}$ is alkyl of one to 4 carbon atoms, inclusive, especially being methyl. Finally, with regard to the sulfonylamino groups described above, $R_{21}$ and $R_{23}$ most preferably exhibit those preferred values as described for carbonylamino groups.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences describe preferred compounds within the scope of each formula of a prostaglandin analog provided herein.

The Chart herein describes the methods whereby the novel prostaglandin analogs of this invention are prepared.

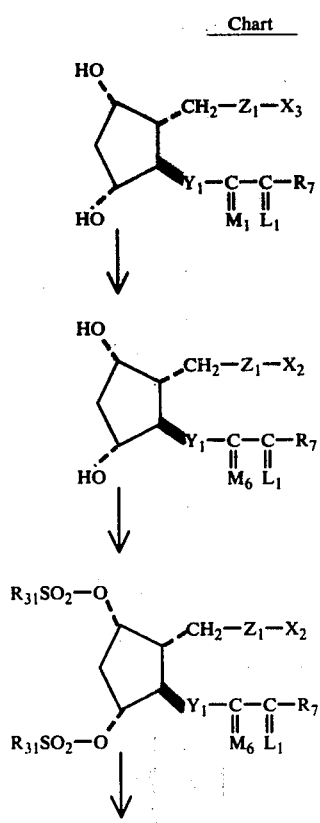

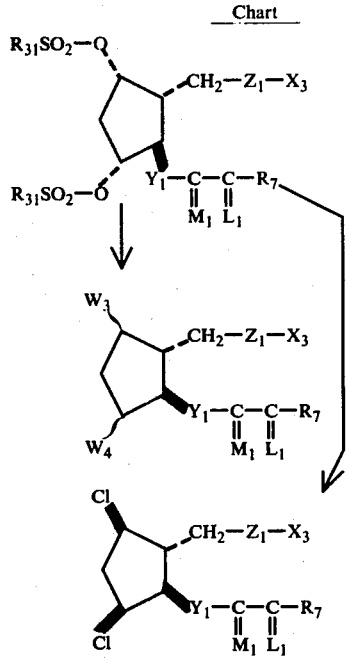

With respect to the chart herein, $L_1$, $M_1$, $R_7$, $Y_1$, and $Z_1$ are as defined above. $M_6$ is the ether-derivatized form of $M_1$ wherein the hydroxyl group of the $M_1$ moiety is replaced by an acetal or silyl blocking group. In particular, acetyl type blocking groups such as tetrahydropyranyl and tetrahydrofuranyl and silyl groups such as t-butyldimethylsilyl are preferably employed. $X_3$ is —$COOR_1$, wherein $R_1$ is as defined above; $CH_2NL_2L_3$, wherein $L_2$ and $L_3$ are as defined above; or —$CH_2OH$. $X_2$ is the similarly derivatized form of $X_3$ when $X_3$ is —COOH or —$CH_2OH$. In these cases $X_2$ represents the corresponding acetal or silyl ester or ether of the respective carboxyl and primary alcohol moieties. When $X_3$ is an ester, or amine, then $X_3$ and $X_2$ are the same.

$R_{31}$ is an alkyl or aryl group such that the corresponding alkyl or aryl sulfonate represents a conventient and readily available moiety employed in the conventional replacement reaction as described in the chart. For example, $R_{31}$ is preferably methyl or p-toluyl, such that the corresponding mesylate (methylsulfonate) or tosylate (p-toluenesulfonate) represents readily accessible derivatives of the hydroxyls.

$W_3$ and $W_4$ are bromo or iodo, being the same.

With respect to the chart, the formula XXI $PGF_\alpha$-type compounds are known in the art and are readily prepared by methods known in the art. These prior art $PGF_\alpha$-type compounds are then selectively blocked at the C-15 position and the C-2 position (in the case of carboxylic free acids and primary alcohols) by first preparing the 9,11-cyclic boronate, thereafter etherifying the resulting bicyclic compound to yield the acetal- or silyl-type compounds, and finally hydrolyzing the cyclic boronate. Procedures for such transformations are described in U.S. Pat. No. 4,016,184, with particular reference to the text accompanying Chart L (column 44) of this patent. Moreover, the patent describes appropriate acetal-type blocking groups and the method of their introduction (see for example the description of column 54 of this patent) and likewise the silyl groups contemplated within the scope of the present process.

Especially preferred are the more stable silyl groups such as t-butyldimethylsilyl.

Having prepared the formula XXII compound, the corresponding bis(alkyl- or arylsulfonate) is then prepared by reaction of the formula XXII compound with the alkyl- or arylsulfonyl chloride corresponding to the bis(alkyl- or arylsulfonate) to be prepared.

Thereafter, the formula XXIII compound is transformed to the formula XXIV compound by hydrolysis of the acetyl- or silyl-type blocking groups. This hydrolysis proceeds under mild acidic conditions, particularly those described in U.S. Pat. No. 4,016,184.

Finally, the formula XXIV intermediate is transformed into the epimerically mixed formula XXV prostaglandin analogs of the present invention by halogen displacement of the bis(alkyl- or arylsulfonate). For preparing the 9,11-bromo or 9,11-iodo-PG-type compounds, the lithium halide, e.g., lithium bromide or lithium iodide corresponding to the 9,11-halo-PG-type compounds to be prepared is employed.

Preferably, the lithium halide is first mixed with dimethylformamide (DMF) and the resulting mixture then combined with the formula XXIV compound. In order to assure a rapid and complete reaction of the formula XXIV intermediate with the lithium halide, elevated reaction temperatures, e.g., 40°–80° C., are employed. Ordinarily reaction times of about one hour are sufficient to yield the equilibrium epimeric-mixture of dibromo and diiodo formula XXV products.

The epimerically mixed products are then recovered and separated by conventional (e.g., chromatographic) means. Following column chromatographic separation, the appropriate stereochemical configuration (i.e., $9\alpha,1$-$1\alpha$-; $9\alpha,11\beta$-; $9\beta,11\alpha$-; or $9\beta,11\beta$-) is assigned based on interpretation of the NMR spectra for each of these products so obtained. Most conveniently, however, appropriate stereochemical configuration for the four products is obtained by correlating the sequence of appearance of the various reaction products with their structure. Due to the difference in rates of formation of each of the various epimeric products, the first product to appear in the reaction mixture will be the $9\beta,11\beta$-epimer; the second will be the $9\beta,11\alpha$-epimer; the third will be the $9\alpha,11\alpha$-epimer; and the fourth will be the $9\alpha,11\beta$-epimer. Thus, monitoring the reaction progress by silica gel thin layer chromatography (TLC), the relative Rf's for each of the products can be determined as they appear in the reaction mixture and used as the basis for assigning the epimeric configuration of pure products obtained by chromatography.

The formula XXIV compound is alternatively converted to the formula XXVI $9\beta,11\beta$-dichloro-PGF-type products by reaction with lithium chloride in the manner described for the preparation of the formula XXV compound from the formula XXIV reaction. However, in the case of the formula XXVI compound, the only product obtained from the reaction mixture will be the single epimer depicted by formula XXVI.

For the preparation of a corresponding $9\alpha,11\alpha$-; $9\alpha,11\beta$-; and $9\beta,11\alpha$-epimer, there is required employment of the $11\beta$-PGF$\beta$-, PGF$\beta$-, or $11\beta$-PGF$\alpha$-compound, respectively, corresponding to the formula XXI PGF$\alpha$ compound. Accordingly, the procedure of the Chart provides for the transformation of such compounds to the various 9,11-dichloro-PGF-type compounds herein.

When the compounds above are prepared as esters and acids are desired, saponification or enzymatic deesterification yields the acid. See U.S. Pat. No. 3,761,356, describing an esterase preparation. For the acids thusly prepared, the corresponding pharmacologically acceptable salts thereof are prepared by neutralization with the base corresponding to the salt to be prepared.

With respect to the novel PG-type amides ($X_1$ is —COL$_3$) and p-substituted phenyl esters ($X_1$ is —COOL$_5$), such compounds are prepared as follows:

With regard to the preparation of the p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides, as the first step in the preparation of amino and cycloamino derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PGF-type carboxylic acids, the corresponding carboxyamides are prepared by one of several amidation methods known in the prior art. See, for example, U.S. Pat. No. 3,981,868, issued Sept. 21, 1976 for a description of the preparation of the present amino and cycloamino derivatives of prostaglandin-type free acids and U.S. Pat. No. 3,954,741 describing the preparation of carbonylamino and sulfonylamino derivatives of prostaglandin-type free acids.

The preferred method by which the present amino and cycloamino derivatives of the PGF-type acids are prepared is, first, by transformation of such free acids to corresponding mixed acid anhydrides. By this procedure, the prostaglandin-type free acid is first neutralized with an equivalent of an amine base, and thereafter reacted a slight stoichiometric excess of a chloroformate corresponding to the mixed anhydride to be prepared.

The amine base preferred for neutralization is triethylamine, although other amines (e.g. pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGF-type free acid is mixed with both the tertiary amine base and the chloroformate in a suitable solvent (e.g. aqueous tetrahydrofuran), allowing the reaction to proceed at $-10°$ to $20°$ C.

Thereafter, the mixed anhydride is converted to the corresponding amino or cycloamino derivative by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about $-10$ to $+10°$ C., until the reaction is shown to be complete. For highly volatile amines, acid addition salts thereof (e.g., methylamine hydrochloride) are employed in place of the corresponding free base (e.g. methylamine).

Thereafter, novel PGF-type amino or cycloamino derivative is recovered from the reaction mixture by conventional techniques.

The carbonylamino and sulfonylamino derivatives of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl of sulfonyl isocyanate, corresponding to the carbonylamino or sulfonylamino derivative to be prepared.

By another, more preferred method the sulfonylamino derivatives of the present compounds are prepared by first generating the PG-type mixed anhydride, employing the method described above for the preparation of the amino and cycloamino derivatives. Thereafter, the sodium salt of the corresponding sulfonamide is reacted with the mixed anhydride and hexamethylphosphoramide. The pure PG-type sulfonylamino derivative is then obtained from the resulting reaction mixture by conventional techniques.

The sodium salt of the sulfonamide corresponding to the sulfonylamino derivative to be prepared is generated by reacting the sulfonamide with alcoholic sodium methoxide. Thus, by a preferred method methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian XL-100, A-60, A-60D, or T-60 spectrophotometer on deuterochloroform solutions with tetramethylsilane as an internal standard (downfield).

Mass spectra are recorded on a CEC model 21-110B Double Focusing High Resolution Mass Spectrometer or an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine" herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

Preparation 1

$PGF_{2\alpha}$, 15-(t-butyl-dimethylsilyl)ether, methyl ester (Formula XXII: $X_2$ is $-COOCH_3$, $Z_1$ is cis$-CH=CH-(CH_2)_3$, $Y_1$ is trans$-CH=CH-$,

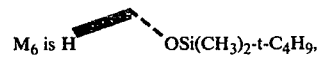

$M_6$ is $H$ $OSi(CH_3)_2$-$t$-$C_4H_9$, $R_3$ and $R_4$ of the $L_1$ moiety are both hydrogen, and $R_7$ is the n-butyl).

A. A solution of $PGF_{2\alpha}$, methyl ester (4.64 g.) is dissolved in 300 ml. of benzene and treated with n-butylboronic acid (1.43 g.) heated to reflux temperature. Water is then removed and the mixture refluxed for an additional 2.5 hours. The resulting solution is then treated with 20 ml. of dimethylformamide and the reaction mixture maintained at reflux temperature for an additional 30 minutes. Thereafter the resulting mixture is cooled to ambient temperature and treated with imidazole (3.4 g.) and t-butyldimethylsilyl chloride (3.77 g.). The benzene is then removed by concentration under reduced pressure at 40° C. and the resulting residue stirred at 35°–40° C. for 12 hours.

B. The reaction product of Part A is then cooled to ambient temperature and treated with acetone (170 ml.), sodium bicarbonate (1.2 g.), and 30% aqueous hydrogen peroxide (35 ml.). This mixture is then stirred at ambient temperature for 5 hours. Thereafter 170 ml. of water is added and the acetone is partially removed by concentration under reduced pressure. The residue thusly obtained and extracted with ethyl acetate in the ethyl acetate extracts are washed with water and dried over magnesium sulfate. The mixture is then filtered and the filtrate concentrated to remove ethyl acetate, yielding 5.97 g. of title product as a colorless oil. Silica gel TLC Rf is 0.68 in ethyl acetate and Skellysolve B (75:25). NMR absorptions are observed at 5.44, 4.35–3.78, 3.63, and 0.87 δ.

Preparation 2

$PGF_{2\alpha}$, 9,11-bis(p-toluenesulfonate), methyl ester (Formula XXIV: $X_2$, $Z_1$, $Y_1$, $L_1$, and $R_7$ are as defined in Preparation 1 and $R_{31}$ is p-toluyl).

$M_1$ is $H$ $OH$.

A. A solution of the reaction product of Preparation 1 (2.41 g.) in pyridine (25 ml.) is treated with p-toluenesulfonyl chloride (7.6 g.), added as a solid. The resulting mixture is then stirred at ambient temperature for 48 hours and the reaction monitored by thin layer chromatography. When the reaction is complete, the resulting mixture is then poured into 125 ml. of water and extracted with diethyl ether (500 ml.). Ethereal extracts have been successively washed with cold 2N aqueous hydrochloric acid and ice until the washings are acidic, potassium bisulfate saturated with sodium chloride, 10% aqueous sodium bicarbonate, and brine. The ethereal layer is then dried over magnesium sulfate, filtered, and concentrated under reduced pressure to remove the diethyl ether, yielding 4.4 g. of crude $PGF_{2\alpha}$, 9,11-bis(p-toluenesulfonate), 15-(t-butyldimethylsilyl) ether, methyl ester. A part of this crude oil (3.83 g.) is then chromatographed on 400 g. of silica gel under pressure. The column is then eluted with 20-25% of ethyl acetate in Skellysolve B, yielding 2.93 g. of pure formula XXIII product as an oil. Silica gel TLC Rf is 0.32 in ethyl acetate and Skellysolve B (25:75). NMR absorptions are observed at 7.58, 4.95, 4.58, 4.04, 3.65 and 0.85 δ.

B. A solution of the reaction product of Part A (3.95 g.) in a mixture of acetic acid:water:tetrahydrofuran (3:1:1, 40 ml.) is stirred at ambient temperature overnight. Water (450 ml.) is added and the resulting mixture is then extracted with diethyl ether. Combined ethereal extracts are then treated with 10% aqueous sodium carbonate and solid sodium carbonate, with stirring in an ice bath. When the mixture becomes neutral or slightly basic, the ethereal and aqueous layers are separated and the aqueous layer is extracted with diethyl ether. The combined ethereal portions are then washed with brine, dried over magnesium sulfate, filtered, and the diethyl ether removed by concentration under reduced pressure to yield 3.35 g. of formula XXIV title product as an oil. Silica gel TLC Rf is 0.27 in ethyl acetate and Skellysolve B (40:60). NMR absorptions are observed at 7.55, 5.35, 4.93, 4.55, 3.94, 2.44, and 0.88 δ.

Preparation 3

$PGF_{2\alpha}$, 9,11-bis(methanesulfonate), methyl ester (Formula XXIV: $X_3$, $Z_1$, $Y_1$, $M_1$, $L_1$, and $R_7$ are as defined above and $R_{31}$ is methyl)

A. A solution of the reaction product of Preparation 1 (2.03 g.) in pyridine (20 ml.) is treated dropwise with methanesulfonyl chloride (2.6 ml.) at ambient temperature. The resulting mixture is then stirred at ambient temperature for three hours, the progress of the reaction being monitored by silica gel TLC. The reaction mixture is then poured into ice water and diethyl ether, and the ethereal layer separated. The aqueous layer is then extracted with diethyl ether and the combined ethereal portions are washed with ice cold 1N hydrochloric acid until acidic, followed by washing with 10% aqueous sodium bicarbonate in water. The ethereal layer is then dried over magnesium sulfate, filtered, and the diethyl ether removed under reduced pressure to yield 2.27 g. of a yellow oil, crude $PGF_{2\alpha}$, 9,11-bis(methanesulfonate), 15-(5-butyldimethylsilyl) ether, methyl ester. This crude formula XXIII product is then chromatographed on 250 g. of silica gel, eluting with 35% ethyl acetate in hexane, yielding 1.84 g. of pure title product. Silica gel TLC Rf is 0.37. NMR absorptions are observed at 5.43, 5.02, 4.77, 4.06, 3.59, 2.98, 2.93, and about 0 δ.

B. Following the procedure of Preparation 2, Part B, the reaction product of Part A above is transformed to pure title product.

Preparation 4

$11\beta$-$PGF_{2\beta}$, 9,11-bis(p-toluenesulfonate), methyl ester

A. Following the procedure of Preparation 2, Part A, $11\beta$-$PGF_{2\beta}$, methyl ester (39.36 g.) is transformed to $11\beta$-$PGF_{2\beta}$, 15-(t-butyldimethylsilyl ether), methyl ester (48.68 g.). Silica gel TLC Rf is 0.30 in acetone and Skellysolve B (1:4). NMR absorptions are observed at 5.76, 5.19, 4.33, 3.73, 3.65, and 0.88 δ.

B. Following the procedure of Preparation 2, the reaction product of Part A (43.7 g.) is transformed to $11\beta$-$PGF_{2\beta}$, 9,11-bis(p-toluenesulfonate), 15-(t-butyldimethylsilyl ether), methyl ester (59.18 g.). Silica gel TLC Rf is 0.60 in ethyl acetate in Skellysolve B (2:3). NMR absorptions are observed at 7.53, 5.46, 5.23, 4.82, 4.63, 4.06, 3.65, 2.44, and 0.83 δ.

C. Following the procedure of Preparation 2, Part B, the reaction product of Part B above (29.18 g.) is transformed to $11\beta$-$PGF_{2\beta}$, 9,11-bis(p-toluenesulfonate), methyl ester (22.86 g.) as a colorless oil which crystallizes on standing. Silica gel TLC Rf is 0.11 in acetone and hexane (1:4). A sample of this crystalline product (1.23 g.) is then recrystallized from diethyl ether and hexane to yield 0.87 g. of white crystals. Melting point is 58°-60° C. Characteristic infrared absorptions are observed at 3580, 1735, 1595, and 1495 $cm^{-1}$. NMR absorptions are observed at 7.53, 5.48, 5.22, 4.80, 3.65, 2.44, and 0.88 δ.

EXAMPLE 1

$9\alpha,11\alpha$-Dibromo-9,11-dideoxy-$PGF_2$, methyl ester; $9\alpha,11\beta$-dibromo-9,11-dideoxy-$PGF_2$, methyl ester; $9\beta,11\alpha$-dibromo-9,11-dideoxy-$PGF_2$, methyl ester; and $9\beta,11\beta$-dibromo-9,11-dideoxy-$PGF_2$, methyl ester (Formula XXV: $X_3$ is —$COCH_3$, $Z_1$ is cis—CH=CH—$(CH_2)_3$—, $W_3$ and $W_4$ are bromo, $Y_1$ is trans—CH=CH—,

$M_1$ is H⟋⟍OH, $R_3$ and $R_4$ of the $L_1$ moiety are both hydrogen, and $R_7$ is n-butyl)

A. Lithium bromide (7.8 g.) is added to dry dimethylformamide (75 ml.) with cooling under nitrogen atmosphere. This mixture is then treated with the title product of Preparation 2 (3.0 g.) in dimethylformamide (15 ml.). The resulting mixture is then heated to 65° C. for one hour under a nitrogen atmosphere. Thereafter, the reaction mixture is cooled to room temperature and poured into 180 ml. of ice water. The aqueous layer is then extracted with diethyl ether and the combined ethereal extracts are washed with water, dried over magnesium sulfate, filtered, and concentrated under reduced pressure to yield a dark yellow oil. A portion of the oil (about two-thirds) is then chromatographed on 132 g. of silica gel using HPLC (high pressure liquid chromatography). The sample is applied to the HPLC column in benzene and elution proceeds with acetone and Skellysolve B (3:17). Thereafter the remaining one-third of the dark red oil is chromatographed under the above HPLC conditions. Further, the partially reacted product obtained from the chromatographic separation is then further reacted with lithium bromide in the manner described above and chromatography yields additional title products herein. Accordingly, the following products are obtained:

B. $9\alpha,11\beta$-dibromo-9,11-dideoxy-$PGF_2$, methyl ester.

C. $9\beta,11\alpha$-Dibromo-9,11-dideoxy-$PGF_2$, methyl ester (650 mg.).

Silica gel TLC Rf is 0.33 in acetone and Skellysolve B (1:4). The high resolution mass spectrum of the trimethylsilyl derivative exhibits a peak at 564.1250. Other peaks are observed at 549, 533, 521, 493, 485, 413, and 333.

D. 9α,11α-Dibromo-9,11-dideoxy-PGF$_2$, methyl ester (168 mg.).

Silica gel TLC Rf is 0.27 in acetone and Skellysolve B (1:4). The high resolution mass spectrum for the trimethylsilyl derivative exhibits a peak at 564.1272 with other peaks as described for the product of Part C.

E. 9β, 11β-Dibromo-9,11-dideoxy-PGF$_2$, methyl ester (220 mg.).

Silica gel TLC Rf is 0.25 in acetone and Skellysolve B (1:4). The high resolution mass spectrum for the trimethylsilyl derivative exhibits a peak at 564.1261 with other peaks as described for the title product of Part C.

Following the procedure of Example 1 there are obtained each of the various formula XXV 9,11-dibromo products as carboxy esters, amides, primary alcohols, or amines, for the various corresponding formula XXIV reactants.

Further following the procedure of Example 1, but employing one of the formula XXIV reactants described above and employing lithium iodide in place of lithium bromide, there are obtained the corresponding formula XXV, 9,11-diiodo products as carboxy esters, amides, primary alcohols, or amines.

EXAMPLE 2

9β,11β-Dibromo-9,11-dideoxy-PGF$_2$

A suspension of 4 g. of Plexaura homomalla (Esper, 1792, Forma S) (Example 1, U.S. Pat. No. 3,761,356) in 40 ml. of water is treated with 9β,11β-dibromo-9,11-dideoxy-PGF$_2$ methyl ester (400 mg.) dissolved in 1.2 ml. of 95% ethanol. The reaction mixture is then stirred at room temperature for 104 hours, after which silica gel TLC Rf (ethyl acetate in Skellysolve B; 3:1) indicates the reaction to be substantially complete. The reaction mixture is then stored at 8° C. for 68 hours. Thereafter the reaction is worked up by the addition of 80 ml. of acetone and then stirring for an additional 30 minutes. The resulting mixture is then filtered and the coral enzyme powder washed with additional acetone. The filtrates are then combined and the acetone removed under reduced pressure. The aqueous residue is then acidified to pH <3 with 10% sodium bisulfate in the presence of diethyl ether. The ethereal layer is then separated and the aqueous layer extracted with diethyl ether. The combined ethereal extracts are then washed with water and brine, dried over magnesium sulfate, filtered, and concentrated under reduced pressure to yield 374 mg. of a pale yellow oil. This oil is then chromatographed on 40 g. of acid washed silica gel, packed with 20% ethyl acetate in Skellysolve B. Eluting with 20-80% ethyl acetate in Skellysolve B, there are obtained 320 mg. of pure title acid. Recrystallization from a mixture of diethyl ether and hexane yields 234 mg. of white crystals. Melting point is 71°-71.5° C. Silica gel TLC Rf is 0.39 in ethyl acetate and Skellysolve B (3:1). Characteristic infrared absorptions are observed at 3320, 2720, 2620, 1705, 1025 and 965 cm$^{-1}$. NMR absorptions are observed at 5.55, 4.40, 4.21, 3.95, and 0.8 δ.

Following the procedure of Example 2, each of the various formula XXV products in methyl ester form, is transformed to the corresponding carboxylic acid.

EXAMPLE 3

9β, 11β-Dichloro-9,11-dideoxy-PGF$_2$, methyl ester (Formula XXVI: X$_3$, Z$_1$, Y$_1$, M$_1$, L$_1$, and R$_7$ are as defined in Example 1)

A solution of lithium chloride (2.11 g.) in dimethylformamide (150 ml.) under nitrogen atmosphere is treated with the title product of Preparation 2 (1.688 g.) in 9 ml. of dimethylformamide. The reaction mixture is then heated at 65° C. for 2.5 hours. Thereafter the resulting mixture is cooled to room temperature and poured into a solution of 75 ml. of saturated aqueous sodium chloride and 300 ml. of water. The aqueous layer is then extracted with diethyl ether and the ethereal extracts are combined and washed with water and brine, dried over magnesium sulfate, filtered, concentrated under reduced pressure to yield 2.06 g. of amber colored oil. The oil is then chromatographed on 150 g. of silica gel, packed with 5% acetone in Skellysolve B. Eluting with 5-10% acetone in Skellysolve B yields 589 mg. of pure title product. Silica gel TLC Rf is 0.56 in 40% ethyl acetate and Skellysolve B. The high resolution mass spectrum of the trimethylsilyl derivative exhibits a peak at 476.2279. Other peaks are observed at 461, 441, 433, 405, 369, and 199. Characteristic infrared absorptions are observed at 3440, 2940, 2860, and 1740 cm$^{-1}$.

B. Following the procedure of Example 2, the title product in methyl ester form (Part A, 300 mg.) is transformed to 214 mg. of the title free acid, which crystallizes on standing. Silica gel TLC Rf is 0.44 in ethyl acetate and Skellysolve B (3:1). The high resolution mass spectrum for the trimethylsilyl derivative is 534.2500. Other peaks are observed at 519, 499, 463, 447, 427, 391, and 199 cm$^{-1}$. Characteristic infrared absorptions are observed at 3360-3000, 2920, 2860, 2660, 1710, 1055, and 1020 cm$^{-1}$. NMR absorptions are observed at 6.39, 5.55, 4.54, 3.61, and 0.89 δ.

EXAMPLE 4

9α,11α-Dichloro-9,11-dideoxy-PGF$_2$, methyl ester and its corresponding free acid A. Following the procedure of Example 3, the title product of Preparation 4 (3.81 g.) is transformed to 1.487 g. of title methyl ester. Silica gel TLC Rf is 0.28 in acetone and Skellysolve B (1:4) and 0.74 in ethyl acetate and Skellysolve B (2:3). The high resolution mass spectrum for the trimethylsilyl derivative exhibits a peak at 476.2279. Other peaks are observed at 461, 441, 433, 405, 369, and 199. Characteristic infrared absorptions are observed at 3440, 2940, 2920, 2860, and 1740 cm$^{-1}$.

B. Following the procedure of Example 2, the title methyl ester of Part A (405 mg.) is transformed to 287 mg. of title free acid, which crystallizes on standing. Recrystallization of title product from diethyl ether in pentane yields 220 mg. of pure free acid as white crystals. Melting point is 40°-42° C. Silica gel TLC Rf is 0.72 is Skellysolve B, ethyl acetate, and acetic acid (10:9:1). The high resolution mass spectrum for the trimethylsilyl derivative exhibits a peak at 519.2299. Other peaks include the molecular ion at 534 and peaks at 499, 491, 483, 463, 447, 435, and 427. Characteristic infrared absorptions are observed at 3400, 3000, 2630, and 1700 cm$^{-1}$.

EXAMPLE 5

9β,11β-Dichloro-9,11-dideoxy-15-methyl-PGF$_2$, methyl ester

A. The titled methyl ester of Example 3 is stored at 8° C. for 250 days, whereupon the resulting substance is chromatographed, eluting with ethyl acetate in Skellysolve B (1:4). There is thereupon obtained 9β,11β-dichloro-9,11-dideoxy-15-dehydro-PGF$_2$, methyl ester.

Silica gel TLC Rf is 0.43 in ethyl acetate and hexane (3:7). Characteristic infrared absorptions are observed at 1740, 1720, 1680, and 1640 cm$^{-1}$. Alternatively, this 15-dehydro-PGF-type compound is obtained by oxidation with 2,3-dichloro-5,6-dicyano-benzoquinone.

B. The reaction product of Part A (1.42 g.) in diethyl ether (300 ml.) is chilled with an ice methanol mixture. The resulting solution is then treated with methyl magnesium bromide in diethyl ether (2.4 ml. of a 2.95 molar solution). The resulting mixture is then stirred at ice bath temperature for 50 minutes, then poured into a cold saturated aqueous ammonium chloride solution. The resulting layers are then separated and the aqueous layer extracted with diethyl ether. The combined ethereal layers are then washed with water, dried over magnesium sulfate, filtered, and concentrated under reduced pressure to yield 1.44 g. of a crude oil. This crude oil is then chromatographed on silica gel, eluting with 20% ethyl acetate in hexane. There is obtained 1.07 g. of pure titled product. Silica gel TLC Rf is 0.41 in ethyl acetate (3:7). The high resolution mass spectrum for the trimethylsilyl derivative yields a peak at 475.2238. A weak molecular ion is observed at 490, and other peaks are observed at 419, 383, 317, and 187.

Following the procedure of Example 3, there are obtained each of the various formula XXVI products from the corresponding formula XXIV reactants. Further, following the procedure of Example 4, there are obtained each of the various 9α,11α-dichloro-PGF products corresponding to the formula XXVI 9β,11β-dichloro-PGF products.

Further, employing PGFβ,9,11-bis(p-toluenesulfonate) there are obtained the corresponding 9α,11β-dichloro-PGF type products corresponding to the formula XXVI 9β,11β-dichloro-PGF type products. Finally, employing 11β-PGFα, 9,11-bis(p-toluenesulfonate), there are obtained each of the various 9β,11α-dichloro-PGF type compounds corresponding to the formula XXVI 9β,11β-dichloro-PGF type products.

Among the novel prostaglandin analogs comprising the instant invention are:

9α,11α-Dichloro-9,11-dideoxy-PGF$_2$, p-benzamidophenyl ester;
9α,11α-Dichloro-9,11-dideoxy-15-epi-PGF$_2$;
2,2-Difluoro-9α,11α-dichloro-9,11-dideoxy-PGF$_2$;
cis-4,5-Didehydro-9α,11α-dichloro-9,11-dideoxy-PGF$_1$;
9α,11α-Dibromo-9,11-dideoxy-15-methyl-PGF$_2$;
9α,11α-Dibromo-9,11-dideoxy-16,16-dimethyl-PGF$_2$;
9α,11α-Dibromo-9,11-dideoxy-16,16-difluoro-PGF$_2$;
9α,11α-Dibromo-9,11-dideoxy-PGF$_2$;
9α,11α-Dichloro-9,11-dideoxy-15-methyl-PGF$_2$;
9α,11α-Dichloro-9,11-dideoxy-16,16-dimethyl-PGF$_2$;
9α,11α-Dichloro-9,11-dideoxy-16,16-difluoro-PGF$_2$; and
9α,11α-Dichloro-9,11-dideoxy-PGF$_2$.

I claim:
1. A prostaglandin analog of the formula

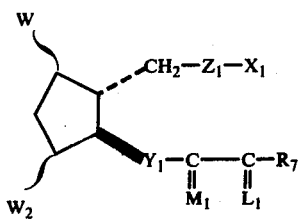

III wherein $W_1$ and $W_2$ are chloro, bromo or iodo, being the same;
wherein $Y_1$ is trans—CH=CH—, —C≡C—, or —CH$_2$CH$_2$—;
wherein $M_1$ is

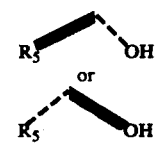

wherein $R_5$ is hydrogen or methyl;
wherein $L_1$ is

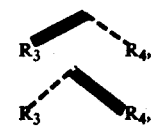

or a mixture of

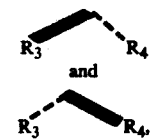

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
 (1) cis—CH=CH—CH$_2$—(CH$_2$)$_g$—CH$_2$—,
 (2) cis—CH=CH—CH$_2$—(CH$_2$)$_g$—CF$_2$—,
 (3) cis—CH$_2$—CH=CH—(CH$_2$)$_g$—CH$_2$—,
 (4) —(CH$_2$)$_3$—(CH$_2$)$_g$—CH$_2$—,
 (5) —(CH$_2$)$_3$—(CH$_2$)$_g$—CF$_2$—,
 (6) —CH$_2$—O—CH$_2$—(CH$_2$)$_g$—CH$_2$—,
 (7) —C≡C—CH$_2$—(CH$_2$)$_g$—CH$_2$—,
 (8) —CH$_2$—C≡C—(CH$_2$)$_g$—$_{CH2}$—,

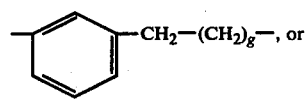

(9)

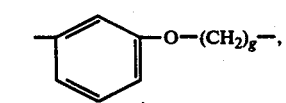

(10)

wherein g is one, 2, or 3;
wherein $R_7$ is
 (1) —(CH$_2$)$_m$—CH$_3$,

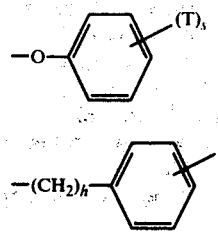

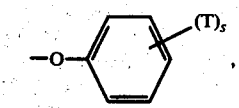

wherein h is zero, one, 2, or 3, inclusive;
wherein m is one to 5, inclusive, T is chloro, fluoro, trifluoromethyl, alkyl of one to 3 carbon atoms, inclusive, or alkoxy of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

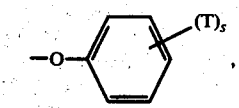

wherein T and s are as defined above, only when $R_3$ and $R_4$ are hydrogen or methyl, being the same or different; and
wherein $X_1$ is
(1) —$COOR_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
(2) —$CH_2OH$,
(3) —$CH_2NL_2L_3$, wherein $L_2$ and $L_3$ are hydrogen, alkyl of one to 4 carbon atoms, inclusive, or —$COOR_1$, wherein $R_1$ is as defined above;
(4) —$COL_4$, wherein $L_4$ is
 (a) amido of the formula —$NR_{21}R_{22}$, wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;
 (b) cycloamido selected from the group consisting of

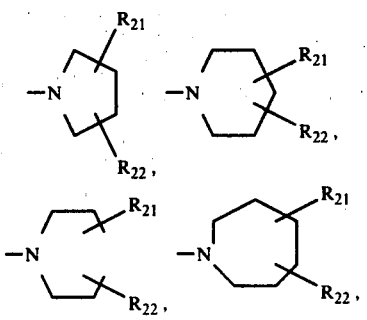

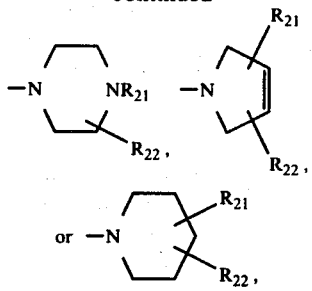

wherein $R_{21}$ and $R_{22}$ are as defined above;
 (c) carbonylamido of the formula —$NR_{23}COR_{21}$, wherein $R_{23}$ is hydrogen or alkyl of one to 4 carbon atoms and $R_{21}$ is as defined above;
 (d) sulphonylamido of the formula —$NR_{23}SO_2R_{21}$, wherein $R_{21}$ and $R_{23}$ are as defined above; or
(5) —$COOL_5$, wherein $L_5$ is p-substituted phenyl selected from the group consisting of

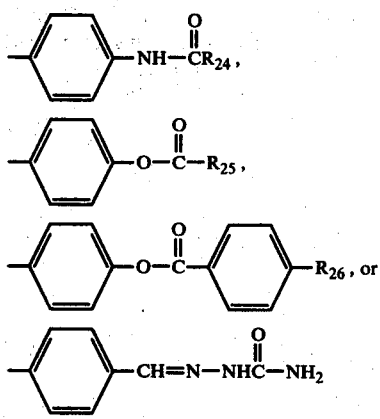

wherein $R_{24}$ is methyl, phenyl, acetamidophenyl, benzamidophenyl, or —$NH_2$; $R_{25}$ is methyl, phenyl, —$NH_2$, or methoxy; and $R_{26}$ is hydrogen or acetamido; with the overall proviso that $Z_1$ is (1), (2), or (3); $R_7$ is (1); and $X_1$ is (1) or (5); only when $Y_1$ is (2) or (3).

2. A prostaglandin analog according to claim 1 wherein $X_1$ is —$COOL_5$.

3. 9α-11α-Dichloro-9,11-dideoxy-PGF$_2$, p-benzamidophenyl ester, a prostaglandin analog according to claim 2.

4. A prostaglandin analog according to claim 1 wherein $X_2$ is —$COOR_1$.

5. A prostaglandin analog according to claim 4 wherein $M_1$ is

6. 9α,11α-Dichloro-9,11-dideoxy-15-epi-PGF$_2$, a prostaglandin analog according to claim 5.

7. A prostaglandin analog according to claim 4 wherein $M_1$ is

8. A prostaglandin analog according to claim 7 wherein $Z_2$ is cis—CH=CH—CH$_2$-(CH$_2$)$_g$—CF$_2$.

9. 2,2-Difluoro-9$\alpha$,11$\alpha$-dichloro-9,11-dideoxy-PGF$_2$, a prostaglandin analog according to claim 8.

10. A prostaglandin analog according to claim 7 wherein $Z_2$ is cis—CH$_2$—CH=CH—(CH$_2$)$_g$—CH$_2$.

11. cis-4,5-Didehydro-9$\alpha$,11$\alpha$-dichloro-9,11-dideoxy-PGF$_1$, a prostaglandin analog according to claim 10.

12. A prostaglandin analog according to claim 7 wherein $Z_2$ is cis—CH=CH—CH$_2$(CH$_2$)$_g$—CH$_2$.

13. A prostaglandin analog according to claim 12 wherein m is 3.

14. A prostaglandin analog according to claim 13 wherein $W_1$ and $W_2$ are bromo.

15. A prostaglandin analog according to claim 14 wherein $R_5$ is methyl.

16. 9$\alpha$,11$\alpha$-Dibromo-9,11-dideoxy-15-methyl-PGF$_2$, a prostaglandin analog according to claim 15.

17. A prostaglandin analog according to claim 14 wherein $R_5$ is hydrogen.

18. A prostaglandin analog according to claim 17 wherein at least one of $R_3$ and $R_4$ is methyl.

19. 9$\alpha$,11$\alpha$-Dibromo-9,11-dideoxy-16,16-dimethyl-PGF$_2$, a prostaglandin analog according to claim 18.

20. A prostaglandin analog according to claim 17 wherein at least one of $R_3$ and $R_4$ us fluoro.

21. 9$\alpha$,11$\alpha$-Dibromo-9,11-dideoxy-16,16-difluoro-PGF$_2$, a prostaglandin analog according to claim 20.

22. A prostaglandin analog according to claim 17 wherein $R_3$ and $R_4$ are both hydrogen.

23. 9$\alpha$,11$\alpha$-Dibromo-9,11-dideoxy-PGF$_2$, a prostaglandin analog according to claim 22.

24. A prostaglandin analog according to claim 13 wherein $W_1$ and $W_2$ are chloro.

25. A prostaglandin analog according to claim 24 wherein $R_5$ is methyl.

26. 9$\alpha$,11$\alpha$-Dichloro-9,11-dideoxy-15-methyl-PGF$_2$, a prostaglandin analog according to claim 25.

27. A prostaglandin analog according to claim 24 wherein $R_5$ is hydrogen.

28. A prostaglandin analog according to claim 27 wherein at least one of $R_3$ and $R_4$ is methyl.

29. 9$\alpha$,11$\alpha$-Dichloro-9,11-dideoxy-16,16-dimethyl-PGF$_2$, a prostaglandin analog according to claim 28.

30. A prostaglandin analog according to claim 27 wherein at least one of $R_3$ and $R_4$ is fluoro.

31. 9$\alpha$,11$\alpha$-Dichloro-9,11-dideoxy-16,16-difluoro-PGF$_2$, a prostaglandin analog according to claim 30.

32. A prostaglandin analog according to claim 27 wherein $R_3$ and $R_4$ are both hydrogen.

33. 9$\alpha$,11$\alpha$-Dichloro-9,11-dideoxy-PGF$_2$, a prostaglandin analog according to claim 32.

* * * * *

UNITED STATES PATENT OFFICE
CERTIFICATE OF CORRECTION

Patent No. 4,140,863   Dated February 20, 1979

Inventor(s) Roy A. Johnson

It is certified that error appears in the above-identified patent and that said Letters Patent are hereby corrected as shown below:

Claim 1 as it appears in the patent should be deleted and the following claim should appear:

1. A prostaglandin analog of the formula

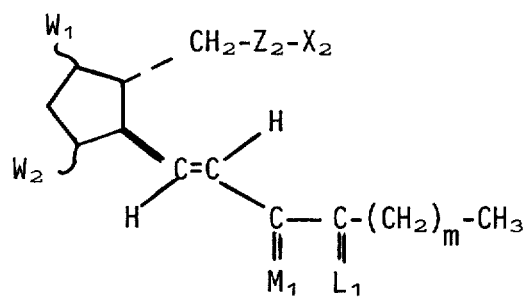

wherein $W_1$ and $W_2$ are chloro, bromo or iodo, being the same;

wherein $M_1$ is 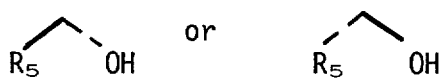

wherein $R_5$ is hydrogen or methyl;

wherein $L_1$ is 

or a mixture of 

wherein $R_3$ and $R_4$ are hydrogen, methyl, or fluoro, being the same or different, with the proviso that one of $R_3$ and $R_4$ is fluoro only when the other is hydrogen or fluoro;

UNITED STATES PATENT OFFICE
CERTIFICATE OF CORRECTION

Patent No. 4,140,863      Dated February 20, 1979

Inventor(s) Roy A. Johnson

It is certified that error appears in the above-identified patent and that said Letters Patent are hereby corrected as shown below:

wherein $Z_2$ is (1) $cis\text{-}CH=CH\text{-}CH_2\text{-}(CH_2)_g\text{-}CH_2\text{-}$, (2) $cis\text{-}CH=CH\text{-}CH_2\text{-}(CH_2)_g\text{-}CF_2\text{-}$, (3) $cis\text{-}CH=CH\text{-}CH_2\text{-}(CH_2)_g\text{-}CH_2\text{-}$, wherein g is one, 2, or 3, wherein m is one to 5, inclusive, wherein $X_2$ is (1) $-COOR_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; or (2) $-COOL_5$, wherein $L_5$ is p-substituted phenyl selected from the group consisting of

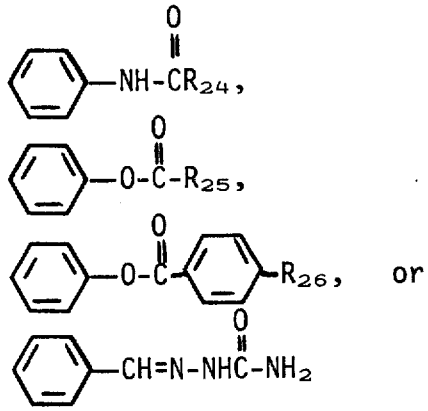

UNITED STATES PATENT OFFICE
CERTIFICATE OF CORRECTION

Patent No. 4,140,863      Dated February 20, 1979

Inventor(s) Roy A. Johnson

It is certified that error appears in the above-identified patent and that said Letters Patent are hereby corrected as shown below:

wherein $R_{24}$ is methyl, phenyl, acetamidophenyl, benzamidophenyl, or $-NH_2$; $R_{25}$ is methyl, phenyl, $-NH_2$, or methoxy; and $R_{26}$ is hydrogen or acetamido.

Column 22, line 48, "9α-11α-" should read -- 9α,11α- --; line 47, "$X_1$" should read -- $X_2$ --;

Column 23, line 10, "$-CH_2(CH_2)_g-CH_2.$" should read -- $-CH_2-(CH_2)_g-CH_2.$ --; line 27, "us fluoro" should read -- is fluoro --.

Signed and Sealed this

*Seventh* Day of *August 1979*

[SEAL]

Attest:

LUTRELLE F. PARKER
*Attesting Officer*     *Acting Commissioner of Patents and Trademarks*